(12) United States Patent
Blomme

(10) Patent No.: US 9,504,468 B2
(45) Date of Patent: Nov. 29, 2016

(54) VASCULAR PROSTHESIS

(75) Inventor: Adri Marinus Blomme, Wapenveld (NL)

(73) Assignee: VASCU-SNAP B.V., Wapenveld (NL)

( * ) Notice: Subject to any disclaimer, the term of this patent is extended or adjusted under 35 U.S.C. 154(b) by 663 days.

(21) Appl. No.: 12/447,164

(22) PCT Filed: Oct. 25, 2007

(86) PCT No.: PCT/NL2007/050511
§ 371 (c)(1),
(2), (4) Date: Jan. 15, 2010

(87) PCT Pub. No.: WO2008/069648
PCT Pub. Date: Jun. 12, 2008

(65) Prior Publication Data
US 2010/0121428 A1    May 13, 2010

(30) Foreign Application Priority Data
Oct. 26, 2006    (NL) ...................... 1032752

(51) Int. Cl.
| | | |
|---|---|---|
| *A61B 17/11* | (2006.01) | |
| *A61F 2/06* | (2013.01) | |
| *A61B 17/00* | (2006.01) | |

(52) U.S. Cl.
CPC ...... *A61B 17/11* (2013.01); *A61B 2017/00862* (2013.01); *A61B 2017/1107* (2013.01); *A61B 2017/1132* (2013.01); *A61B 2017/1135* (2013.01); *A61F 2/064* (2013.01); *A61F 2002/061* (2013.01); *A61F 2002/065* (2013.01)

(58) Field of Classification Search
CPC .......... A61B 17/11; A61B 2017/1107; A61B 2017/1132; A61B 2017/1135; A61F 2/064; A61F 2002/061

USPC ............................ 623/1.14, 1.36; 606/8, 153
See application file for complete search history.

(56) References Cited

U.S. PATENT DOCUMENTS

| | | | | |
|---|---|---|---|---|
| 4,214,587 A | * | 7/1980 | Sakura, Jr. ............. | A61B 17/11 285/239 |
| 4,693,249 A | | 9/1987 | Schenck et al. | |
| 4,728,328 A | * | 3/1988 | Hughes ................. | A61B 17/11 623/1.32 |

(Continued)

FOREIGN PATENT DOCUMENTS

| | | |
|---|---|---|
| EP | 0689806 | 1/1996 |
| WO | WO 2007/029989 | 3/2007 |

OTHER PUBLICATIONS

International Search Report in related International Patent Application No. PCT/NL2007/050511 mailed Feb. 4, 2008.

*Primary Examiner* — Christian Sevilla
*Assistant Examiner* — Seema Mathew
(74) *Attorney, Agent, or Firm* — Kilpatrick Townsend & Stockton LLP

(57) ABSTRACT

A vascular prosthesis comprising a hollow, tubular body (10) having suturing means (20 . . . 22) on at least a first outer end for suturing the body to a vessel wall of a bodily vessel of a user. The suturing means comprise a suturing ring (20), from which at least one suturing member (21) extends radially in order to penetrate the vessel wall. On at least the first outer end the tubular body (10) is double-walled, with an inner wall (11) and an outer wall (12) between which the suturing ring (20) lies enclosed. The suturing ring preferably comprises three such suturing members (21) and a closing ring (40) is arranged locally round the vessel.

7 Claims, 1 Drawing Sheet

(56) References Cited

U.S. PATENT DOCUMENTS

| | | | | |
|---|---|---|---|---|
| 4,930,502 A * | 6/1990 | Chen | | A61B 17/11 606/150 |
| 5,188,638 A * | 2/1993 | Tzakis | | 606/153 |
| 5,486,187 A | 1/1996 | Schenck et al. | | |
| 5,980,567 A * | 11/1999 | Jordan | | A61F 2/064 606/194 |
| 6,030,392 A * | 2/2000 | Dakov | | A61B 17/11 606/139 |
| 6,176,864 B1 * | 1/2001 | Chapman | | A61B 17/11 606/153 |
| 6,248,117 B1 * | 6/2001 | Blatter | | A61B 17/072 606/153 |
| 6,254,642 B1 * | 7/2001 | Taylor | | A61F 2/0004 623/2.1 |
| 6,319,231 B1 * | 11/2001 | Andrulitis | | A61M 1/1037 604/175 |
| 8,621,975 B2 * | 1/2014 | Russo | | A61F 2/852 87/11 |
| 2003/0014064 A1 * | 1/2003 | Blatter | | A61B 17/0644 606/153 |
| 2003/0100910 A1 | 5/2003 | Gifford et al. | | |
| 2003/0212418 A1 | 11/2003 | Yencho et al. | | |
| 2005/0055022 A1 * | 3/2005 | Schubert | | A61B 17/11 606/49 |
| 2005/0125020 A1 * | 6/2005 | Meade | | A61B 17/0401 606/191 |
| 2005/0197664 A1 * | 9/2005 | Blomme | | 606/153 |
| 2008/0109073 A1 * | 5/2008 | Lashinski et al. | | 623/2.1 |
| 2013/0331929 A1 * | 12/2013 | Mitra | | A61L 31/145 623/2.11 |

* cited by examiner

VASCULAR PROSTHESIS

This application is a National Stage Application of PCT/NL2007/050511 and claims priority to Netherlands Application No. 1032752, filed Oct. 26, 2006, the disclosures of the Applications being incorporated herein by reference in their entirety.

The present invention relates to a vascular prosthesis comprising a hollow, tubular body having suturing means on at least a first outer end for suturing the body to a vessel wall of a bodily vessel of a user, wherein the suturing means comprise a suturing ring, from which at least one suturing member extends radially in order to penetrate the vessel wall.

The invention herein relates particularly, though not exclusively, to a vascular prosthesis intended to replace or support the natural vessel wall of a blood vessel, particularly the aorta. Due to damage or other weakening of the vessel wall of a blood vessel a dilation, a so-called aneurysm, can result locally herein. If timely action is not taken the vessel wall can eventually rupture at the location of such an aneurysm, resulting in internal bleeding and therewith a life-threatening situation. To avoid this the blood vessel is functionally replaced by a suitable vascular prosthesis at the location of the aneurysm. Such a prosthesis can also be applied in arteriosclerosis obliterans, and is in this case arranged as by-pass for the original stenosed vessel.

A traditional method of arranging such a vascular prosthesis in the aorta consists of opening the abdominal wall from the sternum to the pubis, whereafter an incision is made along the full length of the blood vessel at the location of the unhealthy part. A suitable vascular prosthesis in the form of a tubular body of circular knitted textile of a similar diameter and length is subsequently sutured to the healthy ends of the blood vessel with suture needle and thread. The affected blood vessel is then preferably placed round the vascular prosthesis and subsequently closed.

A drawback of such a classical approach is that it requires a major operation, which in practice can often require several hours and is thereby particularly radical for the patient. Even more important than the total duration of the operation however is that the blood flow in the blood vessel has to be interrupted for a relatively long time, sometimes more than an hour. This considerable so-called clamp-off time involves a serious danger of complications both during the operation and a long time thereafter. The indicated size of the surgical wound in this operating method will moreover also result in relatively great discomfort for the patient and adversely affect his/her recovery. Despite the open treatment, there is in addition a small risk afterward of a certain leakage along the sutures, resulting in a so-called false aneurysms, which may in such cases necessitate the operation being repeated.

In order to obviate these drawbacks an alternative operation technique has been developed, wherein a vascular prosthesis is arranged in the aneurysm endovascularly. Such an endo-prosthesis generally comprises a tubular body, the wall of which comprises a metal scaffold which is resilient and capable of expanding in radial direction. The endo-prosthesis is arranged in compressed state on a tip of a catheter and manoeuvred with the catheter via a relatively small incision in the groin or another suitable place to the weakened part of the blood vessel for treating. Having arrived at the desired location, a temporary envelope is pulled off the prosthesis, whereby the prosthesis is released and expands from the compressed to an expanded state, wherein the prosthesis lies resiliently against an inner wall of the blood vessel. Initially only the spring force of the scaffold holds the prosthesis in its place in the expectation that, after some time, scar tissue will be deposited on the prosthesis whereby in the long term it will ideally be completely embedded in the wall of the blood vessel.

Such an endovascular method undeniably entails less discomfort for the patient and the circulation of the blood vessels is also maintained. Nevertheless, this method also has drawbacks. Apart from the relatively high cost of this treatment there is the drawback that the suturing of the prosthesis to the blood vessel is effected initially solely by the radial spring force of the prosthesis. There is therefore a real danger that the prosthesis can be entrained by the blood flow and thereby shifts to a greater or lesser degree away from the location for treating. Such a suture moreover entails the risk that blood can find its way between the wall of the blood vessel and the prosthesis and then still exert the original pressure on the vessel wall. Such a case is referred to as an endo-leak. To remedy such a complication a reintervention will follow, or an operation in the traditional manner will still have to be performed.

In order to obviate these and other drawbacks associated with the classical and endovascular treatment, European patent application EP 1.075.231 of applicant describes a vascular prosthesis of the type described in the preamble, whereby a completely new approach is taken. The vascular prosthesis is herein already provided beforehand on at least one of its outer ends with suturing means in the form of a metal suturing ring. The suturing ring comprises at least one suturing member which extends radially therefrom and which is adapted and intended to ultimately penetrate the vessel wall. The prosthesis is fixed in the vessel for treating by means of the suturing ring. This is a relatively simple process which can therefore be performed from a certain distance by a more or less experienced surgeon in an open or laparoscopic procedure.

A limited incision in or close to the affected part of the bodily vessel thus suffices to expose the vessel over a limited length, and only an incision the size of the possibly contracted vascular prosthesis in the vessel wall suffices to enable insertion of the vascular prosthesis into the vessel and internal suturing thereof to healthy ends thereof. Furthermore, by making use of a pre-arranged suturing ring a leakage-proof rapid suture can hereby be achieved, which only requires a minimum clamp-off time of less than the order of ten to fifteen minutes and at least almost precludes endo-leaks. The prosthesis is moreover actually fixed in the vessel wall by means of the suturing ring so that it cannot shift, or hardly so. The discomfort to the patient and a danger of post-operative complications thus remain limited to a minimum. The vascular prosthesis of the type stated in the preamble thus combines the advantages of the classical and the endovascular treatment method, while the associated drawbacks are obviated, or at least significantly reduced.

The presence of metal in the bloodstream can nevertheless result in rejection symptoms and allergic reactions in some patients. The metal suturing ring of the vascular prosthesis of the type stated in the preamble could result in such an undesired reaction in some patients. A first aspect of the present invention has for its object, among others, to provide a vascular prosthesis of the type stated in the preamble in which this drawback is obviated.

Although unavoidable for a reliable suturing to the vessel wall, as in classical suturing, the suturing members of the suturing ring of the vascular prosthesis of the type stated in the preamble inevitably result in damage to the vessel wall.

A further aspect of the present invention has for its object, among others, to limit this damage to the vessel wall.

In order to achieve the intended object, a vascular prosthesis of the type described in the preamble has the feature in a first aspect of the present invention that on at least the first outer end the tubular body is double-walled, with an inner wall and an outer wall, and that the suturing ring lies enclosed between the inner wall and the outer wall, wherein the suturing ring is fully enclosed by the tubular body and the at least one suturing member penetrates the outer wall. The suturing ring thus lies enclosed and covered between the two walls of the tubular body, which is for instance formed from a biocompatible textile and will not provoke the same rejection reactions of the body which many metals do.

The tubular body can be given a double-walled form, at least at the outer end, in order to then receive the suturing ring between the inner wall and the outer wall. Within the scope of the invention it is however also possible to make use of a per se single-walled, tubular body, which is simpler to manufacture from a production engineering viewpoint. For this purpose a particular embodiment of the vascular prosthesis has the feature according to the invention that the tubular body at least substantially comprises a textile sleeve, a wall of which comprises a cuff on at least the first outer end, and that the suturing ring is received in the cuff. The tubular body can herein be folded back in simple manner over the suturing ring once the suturing ring has been arranged over the outer end of the body. A further particular embodiment of the vascular prosthesis has the feature here that the cuff is connected to the sleeve, in particular is sewn thereto, on a side of the suturing ring remote from the outer end. By thus connecting the cuff to the tubular body, the suturing ring is enclosed in the cuff. Such a fixation can be carried out manually or wholly by machine, and pretested.

Although many materials are in principle suitable for the tubular body, a further particular embodiment of the vascular prosthesis according to the invention has the feature that the sleeve is at least substantially composed of a textile of biocompatible fibre, in particular from a group of polyester fibre and polytetrafluoroethylene fibre (PTFE). The sleeve can herein be composed directly from such fibres, although the fibres can also be processed beforehand into a yarn, after which the sleeve is woven, knitted or otherwise formed therefrom. These textile yarns or fibres have proven in practice to be sufficiently liquid-tight and to be accepted by the body.

Diverse materials can also be applied for the suturing ring, although a further particular embodiment of the vascular prosthesis has the feature according to the invention that the suturing ring is composed at least substantially of metal and can be brought from a first compressed state to a second expanded state. A metal ring allows of deformation while retaining strength, and can thus be inserted in compressed state and expanded at the desired location to the final, desired diameter. In this latter state the ring provides a firm basis for the suturing to the vessel for treating.

In a further aspect a vascular prosthesis of the type described in the preamble has the feature according to the invention that three suturing members extend from the suturing ring and that the suturing members are arranged radially at least practically equidistantly on the suturing ring. The invention is based here on the insight that, by thus making use of only three suturing members, minimal damage is inflicted on the vessel wall, while the suturing ring nevertheless obtains an optimal stability. A particularly good suturing is obtained here with a particular embodiment of the vascular prosthesis according to the invention, which is characterized in that the suturing members comprise a spear-shaped outer end. The spear-shaped outer ends of the suturing members are anchored in or beyond the vessel wall, whereby the chance of the suturing ring later being detached under the influence of a liquid flow through the vessel is limited to a minimum.

The suturing members can be formed on the suturing ring in different ways. The suturing members can for instance be cut, or at least released, from an outer wall of the suturing ring and subsequently placed upright. This however costs material in the outer wall of the suturing ring and limits the suturing members in their diameter to a wall thickness of the outer ring. More dimensional freedom is obtained in a further particular embodiment of the vascular prosthesis according to the invention, which is characterized in that the suturing members comprise individually formed elements which are arranged transversely of an outer wall of the suturing ring. The suturing members can thus be designed freely and optimized for their intended suturing action, while this moreover does not detract from the integrity of the outer wall of the suturing ring.

Particularly good results can be achieved with a particular embodiment of the vascular prosthesis according to the invention, which is characterized in that the suturing ring and the suturing members are composed at least substantially of metal.

From a production engineering viewpoint a preferred embodiment of the suturing ring according to the invention has the feature that the suturing ring comprises an at least substantially monolithic body, from which the suturing members extend integrally. The suturing ring is thus manufactured integrally and requires no further assembly or other processing. The vascular prosthesis according to the invention is particularly characterized here in that the suturing ring is composed at least substantially of plastic or metal, in particular is cast therefrom.

For an adequate fixation of the suturing ring, and to support the vessel wall, a preferred embodiment of the vascular prosthesis according to the invention has the feature that the suturing means comprise an annular closing body which is intended and adapted to be received on an outer wall of the bodily vessel at the location of the suturing ring. The closing body is arranged round the vessel at the location of the suturing ring and thus encloses the vessel wall between the suturing ring and the closing body, whereby a penetration of a suturing member into the vessel wall is enhanced and the vessel wall is supported from outside.

In a preferred embodiment the vascular prosthesis is characterized here according to the invention in that the closing body locally comprises at least one inward extending support part, which is intended and adapted to receive therein a suturing member of the suturing ring. The closing body thus supports with the at least one support part on the vessel wall and leaves the vessel wall clear to the sides thereof so as to enhance an uninterrupted blood circulation therethrough. The at least one support part is herein aligned relative to the at least one suturing member of the suturing ring in order to achieve a mutual co-action.

The invention will be further elucidated hereinbelow on the basis of a number of exemplary embodiments and an accompanying drawing. In the drawing.

The figures are purely schematic and not drawn to scale. Some dimensions in particular are shown (highly) exaggerated for the sake of clarity. Corresponding components are designated as far as possible in the figures with the same reference numerals.

Figure 1:
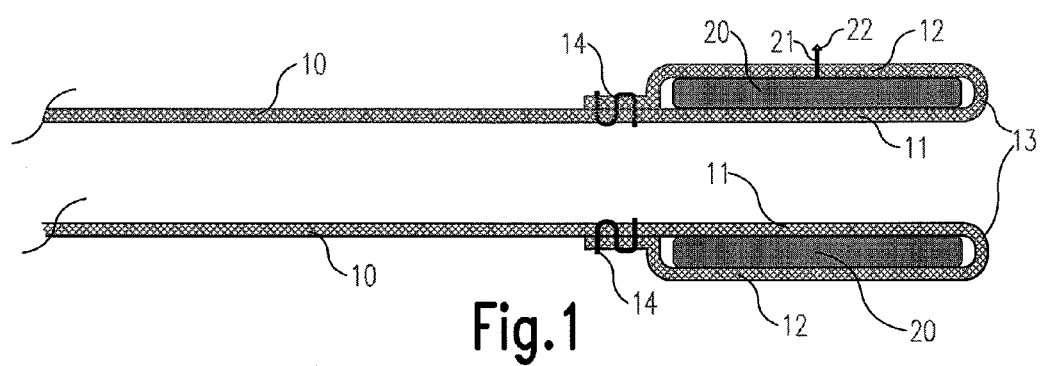
FIG. 1 shows a longitudinal section of a first exemplary embodiment of the vascular prosthesis according to the invention.

The vascular prosthesis of FIG. 1 serves for treating stenosed or dilated blood vessels such as the aorta or the iliac veins, wherein the original blood vessel is respectively bypassed or replaced by the prosthesis. The prosthesis comprises for this purpose a tubular body 10 of a biocompatible fibre, such as polyester or polytetrafluoroethylene fibre (PTFE), which is knitted, woven or otherwise formed to a textile as a sleeve of the desired diameter. Prosthesis 10 is provided with a cuff 13 on at least one outer end, which will eventually be attached proximally in the vessel. The prosthesis is hereby locally double-walled, with an inner wall 11 and an outer wall 12. Lying between inner wall 11 and outer wall 12 is a suturing ring 20 of suturing means which will enable a rapid and reliable suturing of the prosthesis to a vessel wall 31. Suturing ring 20 is thus almost wholly enclosed with the biocompatible textile material of the prosthesis so that it will not cause the body any discomfort. Cuff 13 is closed on a side of suturing ring 20 remote from the outer end by means of a suture 14, which has optionally been arranged manually.

Figure 2:
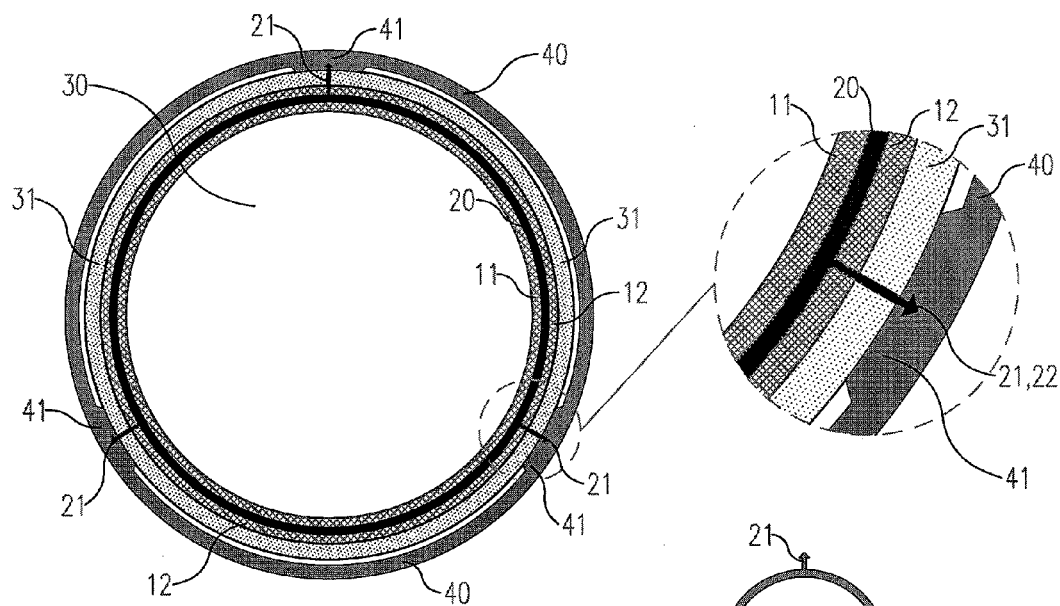
FIG. 2 shows a cross-section of the vascular prosthesis of FIG. 1 in the arranged position.

FIG. 2 shows the prosthesis in a situation where the prosthesis is arranged in an aneurysmal blood vessel 30 in order to support the original vessel wall 31 with prosthesis 10. Prosthesis 10 is optionally introduced laparoscopically into vessel 30 and carried proximally of the aneurysm to a healthy outer end using suturing ring 20. The suturing ring comprises three suturing members 21 with a spear-shaped end 22, which are forced radially into vessel wall 31 at the desired location in order to ensure an adequate suturing of the prosthesis in the vessel wall. The spear-shaped ends 22 herein ensure an efficient anchoring. A closing body 40 is prearranged round blood vessel 30 in order to locally enclose and support the vessel wall. In this example the closing body 40 comprises a number of support parts 41 in order to support therewith on the vessel wall, at least at the location of suturing members 21, while leaving clear the vessel wall therebetween. This avoids the vessel wall being pinched off too much locally as a result of the suturing of the prosthesis to the vessel wall, and on the contrary enhances an uninterrupted circulation of blood through the vessel wall, at least between support parts 41. Support parts 41 moreover serve to receive therein the suturing members 21 with their spear-shaped ends 22 so as to thus firmly anchor the suturing. Closing body 40 can optionally also be additionally provided with such support means between suturing members 21 in order to rest more uniformly on the vessel wall.

Diverse materials can be applied per se for suturing ring 20. Good experiences have been had with a metal suturing ring of a not or hardly (still) oxidizing metal, although a suitable plastic can also be applied within the scope of the invention. The suturing members can be formed individually and arranged only later on an outer surface of suturing ring 20, although it is also possible as here to make use of a monolithic body of metal or plastic, which has for instance been formed integrally by casting or by means of a material-removing process. Suturing members 21 then form an integral whole with the other part of suturing ring 20.

Figure 3:
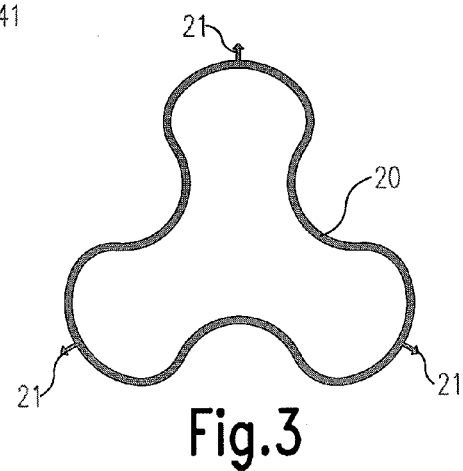
FIG. 3 shows a cross-section of the suturing ring of the vascular prosthesis of the foregoing figures in compressed state.

Use is advantageously made of a suturing ring 20 as shown in FIG. 3 which is introduced in the shown compressed state and expanded in situ to form the final annular, expanded state of FIG. 2 at the location of the suturing to be realized. Metals are generally suitable for such contraction and expansion, although this can also be applied in plastics, wherein a temporary fixation member holds the ring together under tension in the compressed state.

Although the invention has been further elucidated above on the basis of only a single embodiment, it will be apparent that the invention is by no means limited thereto. On the contrary, many variations and embodiments are still possible within the scope of the invention for a person with ordinary skill in the art. In addition to use for the stated and other blood vessels, the invention can also be applied for other bodily vessels in which a bypass or partial replacement must be realized.

The invention claimed is:

1. Vascular prosthesis comprising an artificial hollow, tubular body extending between a first extreme end and a second extreme end and comprising a first extreme end portion at said first extreme end which is provided with suturing means configured for suturing said first extreme end portion of said artificial tubular body to a vessel wall of a blood vessel of a user, wherein the suturing means comprise a suturing ring with at least one radially extending suturing member configured to penetrate said vessel wall during operation, wherein said suturing ring comprises a complete, closed substantially ring shaped body carrying a number of radially extending suturing members, wherein said tubular body comprises a textile sleeve of a textile of bio-compatible fibre having a double walled first extreme end portion which fully encloses said suturing ring between an inner wall and an outer wall of said double walled end portion, wherein the suturing means further comprise an annular closing body which is configured to support the vessel wall while surrounding said suturing ring and said vessel, wherein the suturing ring is in a compressed first state and can be deployed from said compressed first state to an expanded second state, wherein said suturing members are configured to penetrate through and radially project from said double walled end portion of said textile sleeve to be received by said vessel wall and said annular closing body in said expanded second state of said suturing ring, wherein a wall of said textile sleeve comprises a cuff on at least said first extreme end portion and the suturing ring is encapsulated and fixed in said cuff, wherein said cuff is sewn to the sleeve on a side of the suturing ring remote from said first extreme end.

2. Vascular prosthesis as claimed in claim 1, wherein the suturing ring comprises three projecting suturing members which are arranged at least substantially equidistantly.

3. Vascular prosthesis as claimed in claim 1, wherein the suturing members each comprise a spear-shaped extreme end.

4. Vascular prosthesis as claimed in claim 1, wherein the suturing ring comprises a monolithic body, from which the suturing members extend integrally.

5. Vascular prosthesis as claimed in claim 4, wherein the suturing ring is cast at least substantially of plastic or metal.

6. Vascular prosthesis as claimed in claim 1, wherein the closing body locally comprises at least one inward extending support part, which is intended and adapted to receive therein a suturing member of the suturing ring.

7. Vascular prosthesis according to claim 1 wherein said textile sleeve is made of a bio-compatible fibre from a group of polyester fibre and polytetrafluoroethylene fibre (PTFE).

* * * * *